United States Patent [19]

Mikhail

[11] Patent Number: 5,480,448
[45] Date of Patent: Jan. 2, 1996

[54] ACETABULAR CUP GROOVE INSERT

[76] Inventor: W. E. Michael Mikhail, 4203 Shamley Green, Toledo, Ohio 43623

[21] Appl. No.: 233,296

[22] Filed: Apr. 26, 1994

Related U.S. Application Data

[63] Continuation-in-part of Ser. No. 129,956, Sep. 20, 1993, abandoned.

[51] Int. Cl.$^6$ ........................................................ A61F 2/34
[52] U.S. Cl. .................................................. 623/22; 623/18
[58] Field of Search .................................. 623/16, 17, 18, 623/19, 20, 22, 23

[56] References Cited

U.S. PATENT DOCUMENTS

| | | | |
|---|---|---|---|
| 3,829,904 | 8/1974 | Ling et al. | |
| 3,986,212 | 10/1976 | Sauer | |
| 4,040,131 | 8/1977 | Gristina | |
| 4,281,420 | 8/1981 | Raab | |
| 4,296,714 | 10/1981 | Buchner | 123/53 B |
| 4,380,090 | 4/1983 | Ramos | |
| 4,491,987 | 1/1985 | Park | |
| 4,596,580 | 6/1986 | Weill | 623/22 |
| 4,695,282 | 9/1987 | Forte et al. | 623/22 |
| 4,704,127 | 11/1987 | Averill et al. | 623/22 |
| 4,883,490 | 11/1989 | Oh | 623/22 |
| 4,904,267 | 2/1990 | Bruce et al. | 623/23 |
| 4,997,447 | 3/1991 | Shelley | 623/22 |
| 5,002,577 | 3/1991 | Bolesky et al. | 623/22 |
| 5,009,665 | 4/1991 | Serbousek et al. | 623/22 |
| 5,009,666 | 4/1991 | Van Syckle et al. | 623/18 |
| 5,019,105 | 5/1991 | Wiley | 623/22 |
| 5,021,062 | 6/1991 | Adrey et al. | 623/22 |
| 5,021,063 | 6/1991 | Tager | 623/23 |
| 5,049,158 | 9/1991 | Engelhardt et al. | 623/22 |
| 5,080,677 | 1/1992 | Shelley | 623/22 |
| 5,092,897 | 3/1992 | Forte | 623/22 |
| 5,171,243 | 12/1992 | Kashuba et al. | 606/86 |
| 5,171,285 | 12/1992 | Broderick | 623/22 |
| 5,171,286 | 12/1992 | Lawes et al. | 623/22 |
| 5,176,711 | 1/1993 | Grimes | 623/22 |
| 5,181,926 | 1/1993 | Koch et al. | 623/22 |
| 5,192,329 | 3/1993 | Christier et al. | 623/22 |
| 5,197,989 | 3/1993 | Hinckfuss et al. | 623/23 |
| 5,222,984 | 6/1993 | Forte | 623/22 |
| 5,226,917 | 7/1993 | Schryver | 623/22 |

FOREIGN PATENT DOCUMENTS

| | | |
|---|---|---|
| 0065482A2 | 11/1982 | European Pat. Off. . |
| 0091315A1 | 10/1983 | European Pat. Off. . |
| 253941A | 1/1988 | European Pat. Off. . |
| 0313773A1 | 5/1989 | European Pat. Off. . |
| 2649005A1 | 1/1991 | France . |
| 2154141 | 9/1985 | United Kingdom ............ 623/22 |

OTHER PUBLICATIONS

Catalog of Osteonics Corp., 59 Route 17, Allendale, N.J. entitled "Cemented Acetabular Cup—Surgical Protocol", copyright 1992.
Catalog of Howmedica International entitled "Exeter Total Hip System" (date of publication unknown).
The following articles from vol. 19, No. 3, Jul. 1988 entitled "The Orthopedic Clinics of North America—Long-Term Results of Cemented Joint Replacement" published by W. B. Saunders Company, Philadelpha, Pa.: (a) N. Eftekhar et al., Incidence and Mechanisms of Failure of Cemented Acetabular Component in Total Hip Arthoplasty, pp. 557–566; (b) C. Ranawat et al., Effect of Modern Cement Technique on Acetabular Fixation Total Hip Arthroplasty, pp. 599–603; (c) B. M. Wroblewski, Wear and Loosen of the Socket in the Charnley Low–Friction Arthoplasty, pp. 627–636; (d) M. D. Fuchs et al., Results of Acetabular Revisions with Newer Cement Techniques, pp. 649–655.

*Primary Examiner*—David Isabella
*Attorney, Agent, or Firm*—Emch, Schaffer, Schaub & Porcello Co.

[57] ABSTRACT

An acetabular cup assembly having a non-metallic inner cup to be positioned within a metal shell with a dome shaped interior surface. The non-metallic inner cup is formed with a plurality of interconnecting grooves and ribs. The ribs are configured to contact the interior surface of the metal shell while the grooves have inner surface areas spaced from the interior surface of the metal shell. The combination of the ribs and the groove define cavitites in the outer surface of the inner cup. The assembly further includes groove insert members that are configured to be positioned in and filling substantially all of the cavities.

20 Claims, 12 Drawing Sheets

ACETABULAR CUP GROOVE INSERT

CROSS-REFERENCE TO RELATED APPLICATION

This application is a continuation-in-part of my U.S. application, Ser. No. 08/129,956, filed Sep. 20, 1993, now abandoned.

BACKGROUND ART

The present invention relates to an acetabular cup for receiving the ball of a femoral hip joint prosthesis.

Acetabular cups and acetabular cup assemblies of various types have long been used in hip joint replacement surgery. In such surgery, a femoral hip joint prosthesis formed of a suitable metal such as a cobalt chrome molybdenum alloy or other FDA approved material is implanted in the femur. The femoral hip joint prosthesis has an associated spherical-shaped ball. It is necessary to implant an acetabular cup or acetabular cup assembly in the acetabulum in a cavity which has been prepared by the surgeon for the purpose of receiving the spherical-shaped ball.

The artificial socket (i.e., acetabular cup or acetabular cup assembly) in which the ball of the femoral hip joint prosthesis is to be positioned is formed of a material other than metal and is frequently formed of a suitable biocompatible plastic such as a high molecular weight polyethylene (HMWPE) as this provides a natural lubricity which permits the ball to freely rotate in the cup socket.

In some instances, the acetabular cup is a single unitary device which is implanted in a prepared cavity of the acetabulum using a suitable bone cement such as polymethlymethacrylate (PMMA). In other instances, depending upon the condition of the patient and/or the preference of the surgeon, an acetabular cup assembly consisting of multiple units including a metal shell and a plastic cup-shaped insert may be used. In the latter instance, the metal shell may be affixed in the prepared cavity of the acetabulum by a variety of means including screws joining the metal shell directly to the acetabulum or a friction fit in the cavity with a shell having an exterior surface of a type which is roughened, coated or formed with interstices which will promote bone ingrowth therein. Examples of one-piece acetabular cups are shown in U.S. Pat. Nos. 3,829,904; 3,986,212 and the FIG. 1 embodiment of U.S. Pat. No. 5,009,665. Examples of multiple-piece acetabular cup assemblies are shown in the FIGS. 2-4 embodiments of U.S. Pat. No. 5,009,665 and in U.S. Pat. Nos. 4,704,127; 4,695,282; 5,002,577 and 5,019,105. The foregoing prior art patents are hereby incorporated by reference in this application.

Heretofore, plastic cup members intended for use as a single unitary unit were manufactured to one of various designs depending upon the manufacturer and plastic cup members intended for use with a separate shell member to form an acetabular cup assembly were designed and manufactured to different configurations even in those instances where a single manufacturer produced both the unitary type and the multiple component assembly type of acetabular cup prosthesis. This, of course, required that the manufacturer have one mold for forming a plastic member intended for the unitary acetabular cup prosthesis and a different mold for forming the plastic cup member of the same size intended for use with a metal shell for an acetabular cup assembly. As is well known, the plastic acetabular cups come in a wide variety of sizes and a separate mold is required for each size cup. Heretofore, the fact that different designs of plastic acetabular cups were used for unitary acetabular cup prostheses than for acetabular cup assemblies required that the hospital carry separate inventories of plastic cups, one set for the unitary version and a second set for the multiple component version, with several sizes required for each such set.

DISCLOSURE OF THE INVENTION

My parent application, Ser. No. 08/129,956 filed Sep. 20, 1993 discloses a plastic acetabular cup member which is suitable for use either in direct cemented implantation with the bone or as an insert for a metal shell component of an acetabular cup assembly. Since the same plastic cup member may be used either as a single element acetabular cup prosthesis cemented in the prepared cavity of the acetabulum or as a component with a metal shell affixed in the prepared cavity of the acetabulum, the hospital is required to carry only one type of plastic acetabular cup member for each size rather than two.

The acetabular cup member is provided with an exterior surface having irregularities such as grooves and ribs which permits its use as a unitary prosthesis in a prepared cavity of an acetabulum, in which event it is retained therein by bone cement in direct contact with such unitary acetabular cup member.

As may be appreciated, when the acetabular cup member is used in combination with a metal shell component, the exterior surfaces which are in contact with the interior surface of the metal shell will be subjected to compressive forces imparted by the weight of the patient in whom it is implanted. Such compressive forces will be of variable magnitude at various portions of the interface between the interior surface of the metal shell and the exterior surfaces of the acetabular cup member such as the outermost portions of the ribs which are in contact with the interior surface of the metal shell. The compressive forces thus imparted may cause the plastic material of the acetabular cup member to creep and thereby deform the ribs causing cold flow of plastic partially into the grooves between the ribs. The present invention is directed to a pre-molded groove insert which is intended for use with the acetabular cup member having surface irregularities such as ribs and grooves when such cup member is intended for use in combination with a metal shell but which is designed to be readily removed from the acetabular cup member in those instances when the acetabular cup member is intended to be implanted directly in the prepared cavity of an acetabulum with bone cement, Accordingly, it is an object of the present invention to provide an acetabular cup groove insert for use in combination with a plastic acetabular cup member having grooves or similar surface irregularities.

It is a further object of the present invention to provide an acetabular cup prosthesis having a plastic acetabular cup member which along with a groove insert may be used in combination with a metal shell affixed in a prepared cavity of an acetabulum but which is suitable for use in direct cemented implantation in a prepared cavity of an acetabulum when used without a groove insert.

Other objects and advantages of the present invention will become readily apparent from the following detailed description of the drawings.

BEST MODE OF CARRYING OUT INVENTION

Figure 1:
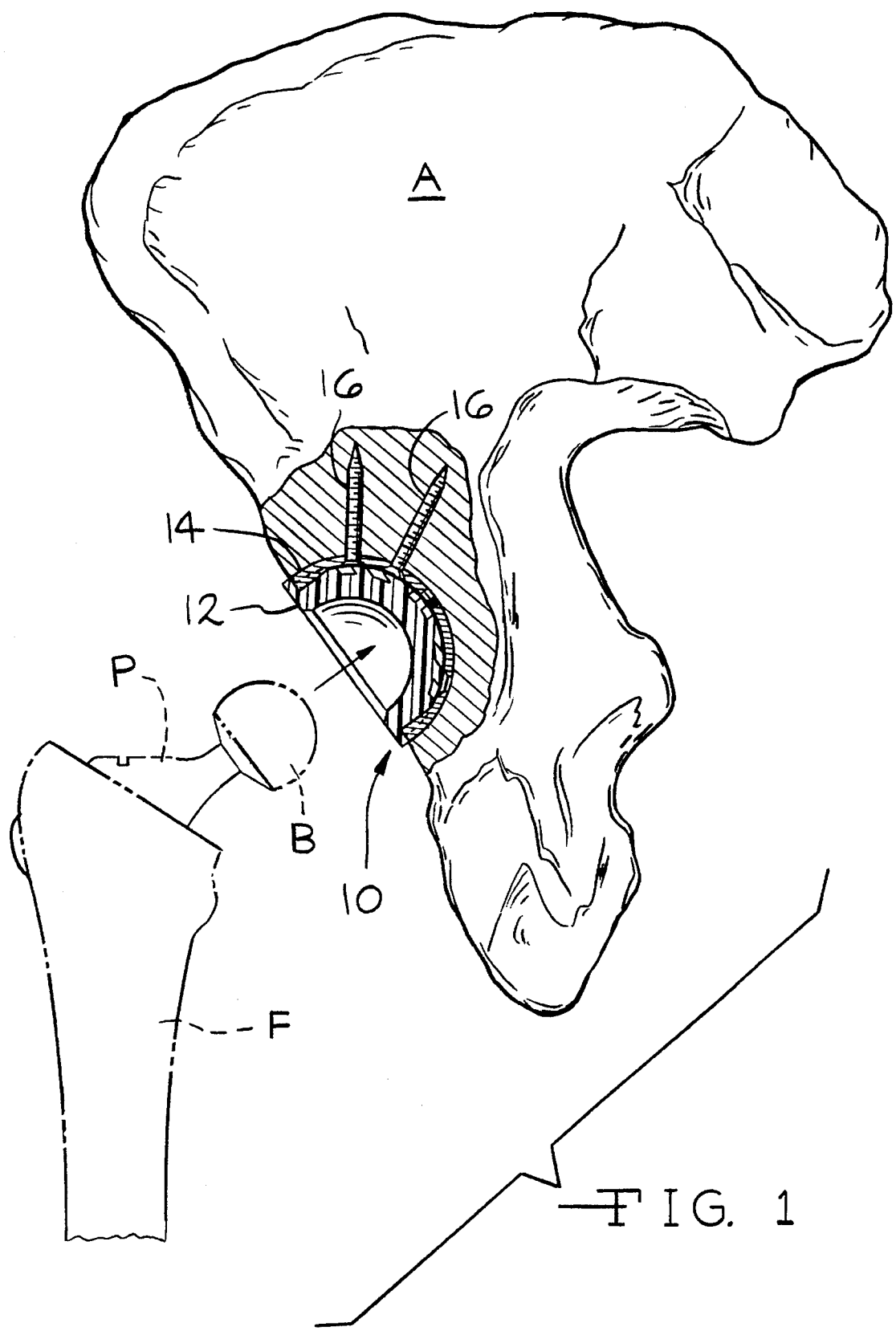
FIG. 1 is a schematic view showing one version of the present invention with a metal shell affixed by screws in a prepared cavity of the acetabulum and with the acetabular cup member positioned therein ready to receive a spherical ball of a femoral hip joint prosthesis.

Referring now to FIG. 1, there is shown an acetabulum A in which has been implanted an acetabular cup assembly generally designated by the numeral 10. The acetabular cup assembly 10 shown in FIG. 1 includes an acetabular cup member 12 which is preferably formed of a polymer such as HMWPE but which may also be formed of a ceramic or other suitable non-metallic material. The acetabular cup member 12 is assembled to a metal shell 14 which is affixed in a prepared cavity of the acetabulum by two or more screws 16.

The acetabular cup member 12 is shown as being prepared to receive a spherical ball B of a femoral hip joint prosthesis P which has been implanted in a femur F.

Figure 2:
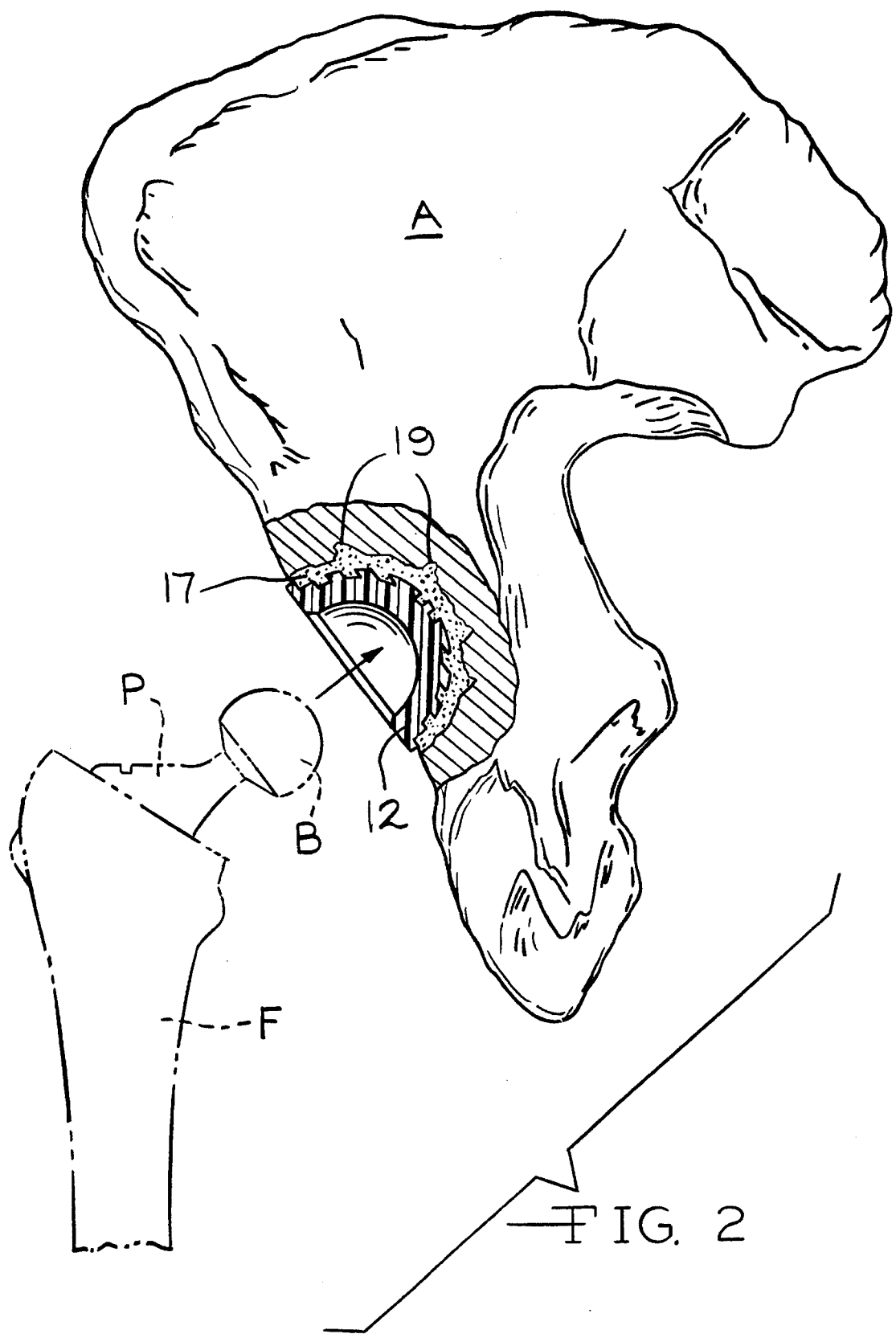
FIG. 2 is a view similar to FIG. 1 showing a unitary acetabular cup member of the present invention affixed directly in a prepared cavity of the acetabulum with bone cement.
Figure 3:
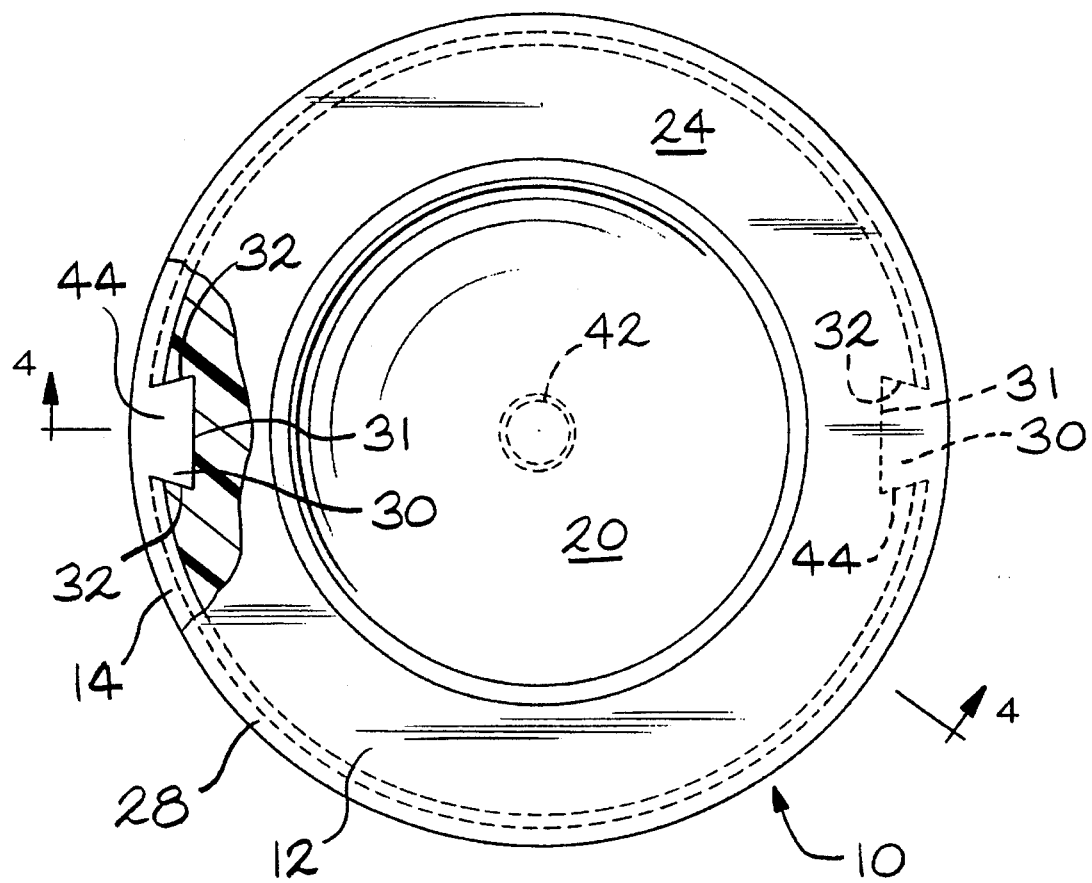
FIG. 3 is a plan view, partly in section, of the acetabular cup assembly of FIG. 1.
Figure 4:
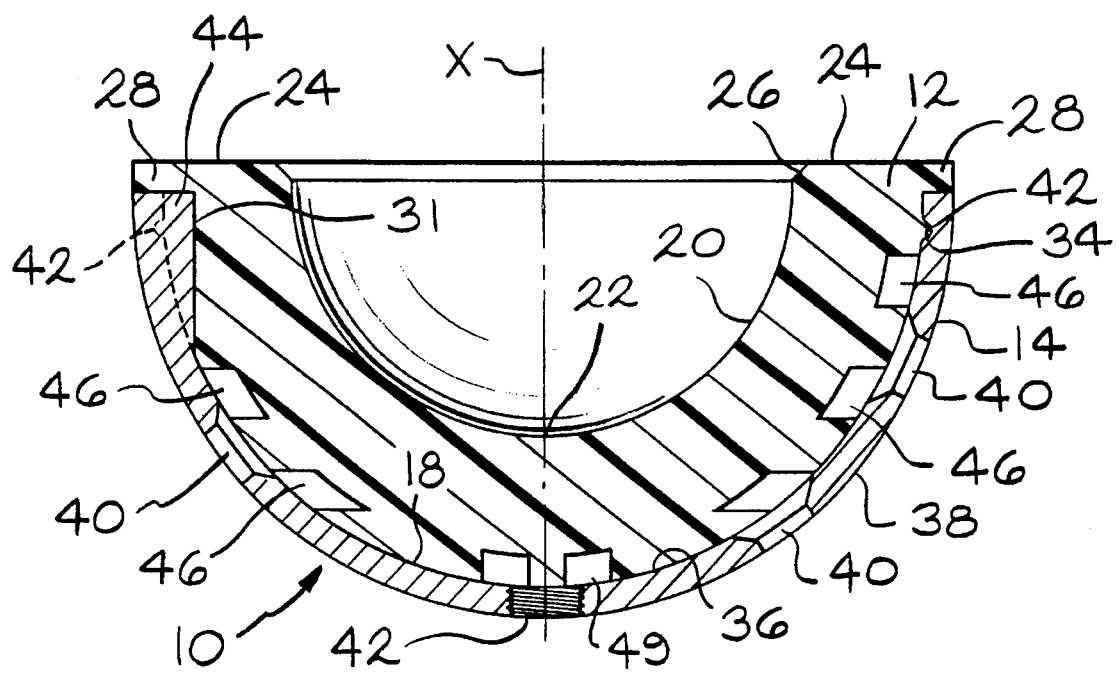
FIG. 4 is a view taken through line 4—4 of FIG. 3.

FIG. 2 shows the identical plastic acetabular cup member 12 functioning as a unitary prosthesis and implanted directly in the prepared cavity of the acetabulum A with bone cement 17. The cavity preferably has been formed with irregularities 19 to provide for good retention of the bone cement 17.

Referring now to FIGS. 3–7, the acetabular cup member 12 of the present invention includes an exterior face 18 and an interior face 20. The acetabular cup member 12 is symmetrical about an axis X. The interior face 20 is smooth and has a major portion having a spherical configuration with an apex 22 lying on the axis X. The acetabular cup member 12 includes a planar edge 24 which is joined to the spherical-shaped interior face 20 by a chamfer 26. Preferably, the spherical portion of the interior face 20 is a full hemisphere. Preferably, the planar edge 24 extends beyond the exterior face 18 to form a flange 28 which, extends annularly around the exterior face 18. Under this embodiment, there are provided both means for engaging the acetabular cup member 12 to the metal shell 14 when the cup member 12 is used as an element of an acetabular cup assembly 10 and means for engagement of the cup member 12 by bone cement when it is used as a unitary prosthesis.

The means for affixing the cup member 12 to a metal shell 14 comprise a pair of dovetail slots 30 each having a rear wall 31 extending substantially parallel to the axis X and a pair of side walls 32 angling with respect to one another such that they are spaced further apart at their respective points of juncture with the rear wall 31 and taper inwardly towards each other in a direction away from such rear wall. The exterior face 18 is also provided with an outwardly extending bead 34 spaced below the edge 24 and its flange 28 and, except for the area of the dovetail slots 30, extending completely around the exterior face 18 in that area.

The metal shell 14 is cup-shaped and has a smoothly polished interior face 36 with a configuration designed to snugly receive the outermost portion of the exterior face 18 of the acetabular cup member 12. The shell 14 also has an exterior face 38 substantially parallel to the interior face 36 and has a plurality of apertures 40 for receiving the screws 16. The shell 14 also has a threaded aperture 42 at its apex along the axis X which may be used for insertion in the prepared cavity or for extraction in the event subsequent revision surgery is required. The metal shell 14 is provided with an annular groove 42 for receiving the bead 34 of the acetabular cup member 12 and a pair of dovetail-shaped ribs 44 intended to be positioned and sized to be received in the dovetail slots 30 of the acetabular cup member 12.

Figure 5:
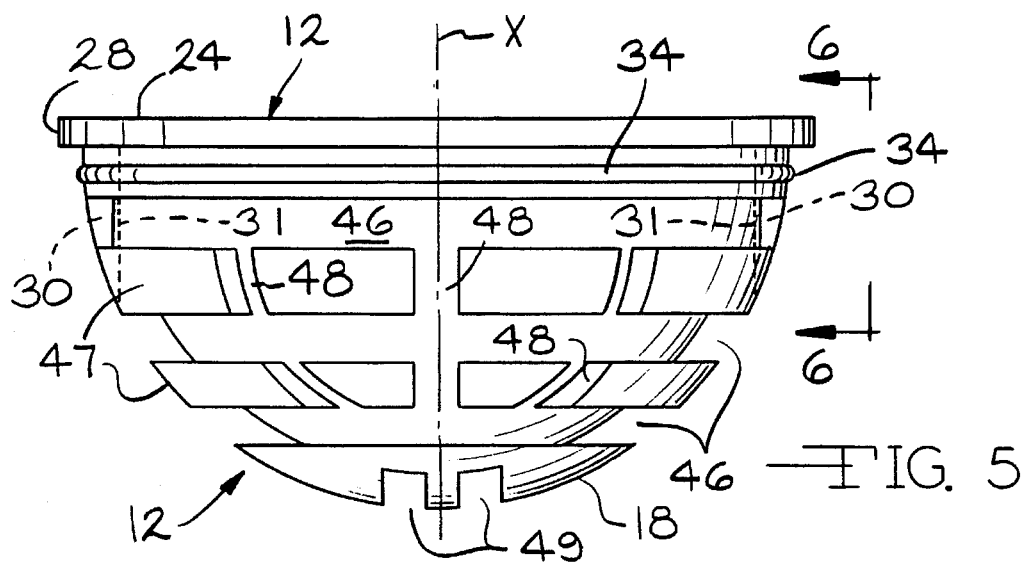
FIG. 5 is an elevational view of the acetabular cup member which is usable either with the shell as shown in FIG. 1 or as a unitary prosthesis as shown in FIG. 2.
Figure 7A:
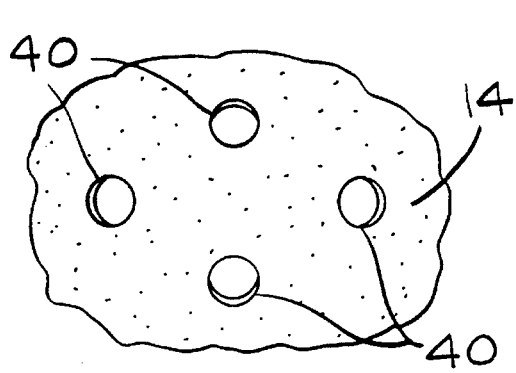
FIG. 7A is a fragmentary view looking in the direction of line 7A—7A of FIG. 7.
Figure 6:
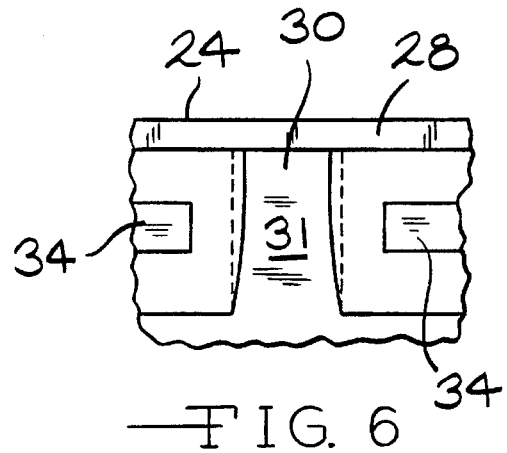
FIG. 6 is an enlarged fragmentary view of the plastic acetabular cup member looking in the direction of line 6—6 of FIG. 5 and showing a dovetail groove which can be engaged by a corresponding dovetail rib of a metal shell when used as a component of a multiple unit acetabular cup assembly.
Figure 7:
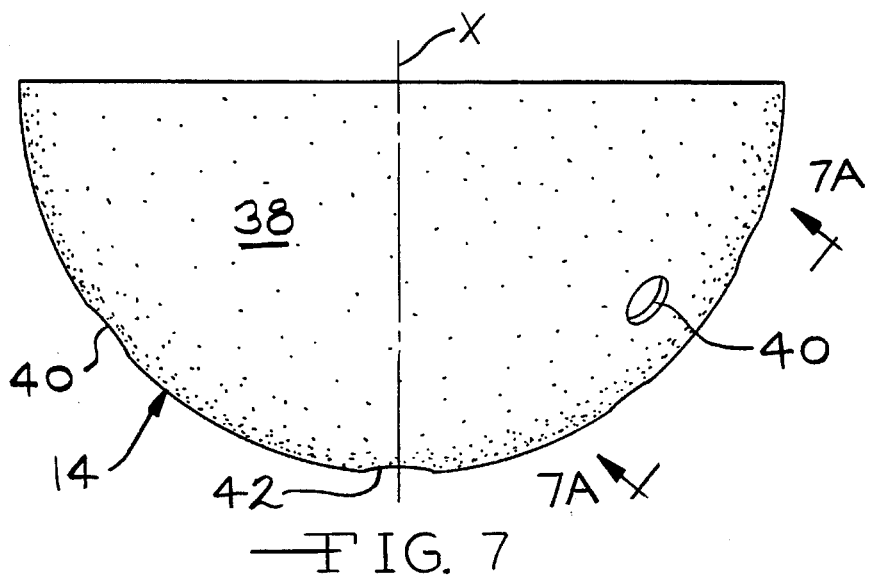
FIG. 7 is an elevational view of a metal shell of the type shown in FIG. 4.

Referring particularly to FIG. 5, there is shown one type of means for engaging the acetabular cup member 12 in bone cement when it is used as a unitary prosthesis, There are provided three rows of annular grooves 46 which are substantially perpendicular to the axis X and are separated by ribs 47. Additionally, the rows of grooves 46 may be joined together by grooves 48 extending toward the apex 22 and defining planes which extend through the axis X. Additional grooves 49 may be formed therein adjacent the apex of the exterior face 18.

As can be seen in FIG. 2, when the acetabular member 12 is used as a unitary prosthesis without the metal shell, the bone cement 17 fills in the grooves 46, 48 and 49 and serves to retain the acetabular cup member 12 in the cavity formed in the acetabulum A.

Figure 8:
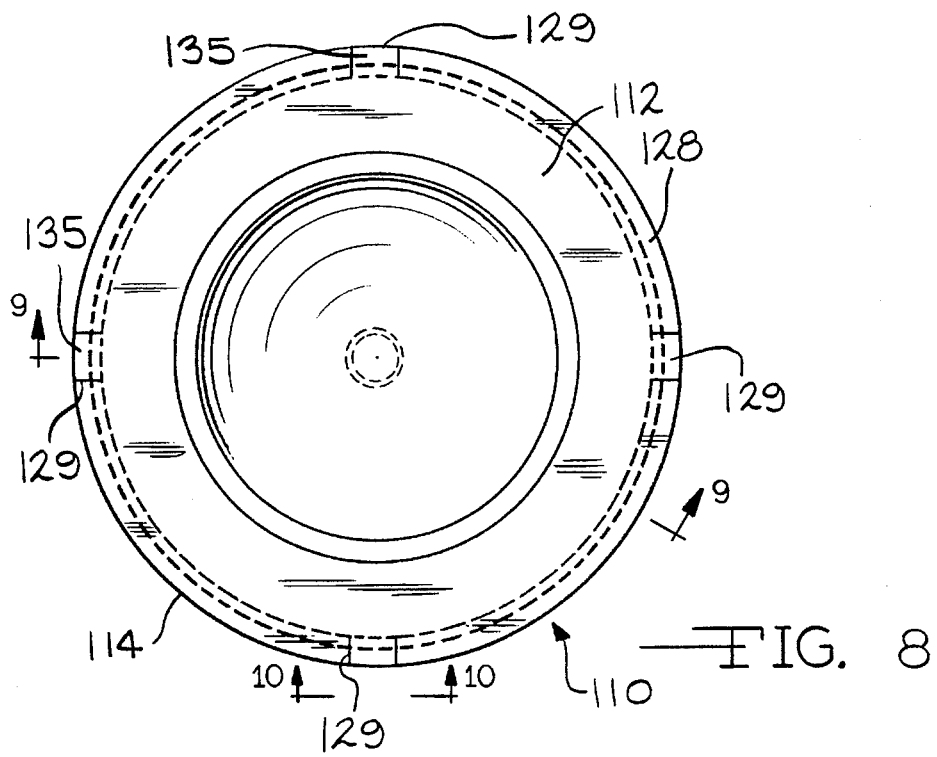
FIG. 8 is a plan view of another embodiment of an acetabular cup member showing it assembled with a metal shell.
Figure 9:
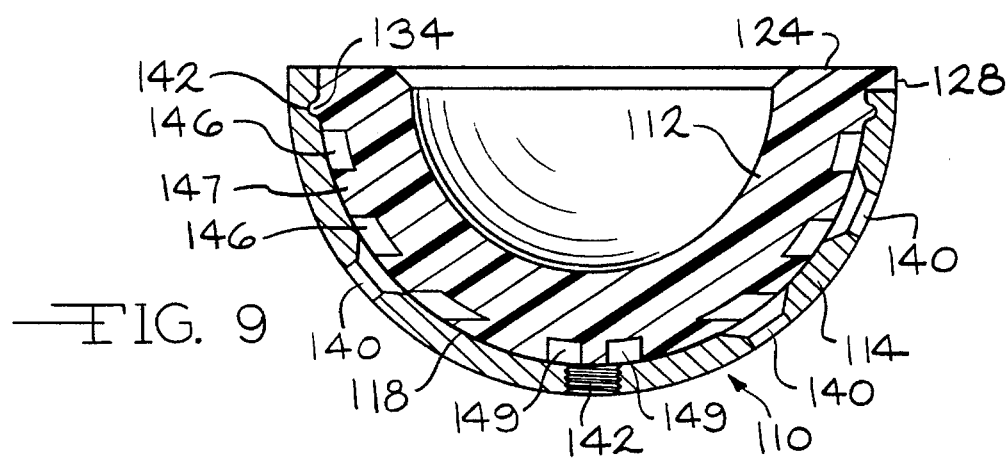
FIG. 9 is a sectional view taken through line 9—9 of FIG. 8.
Figure 10:
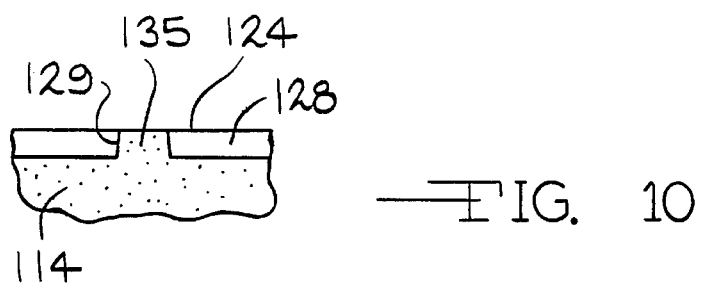
FIG. 10 is an fragmentary view looking in the direction of line 10—10 of FIG. 8.
Figure 11:
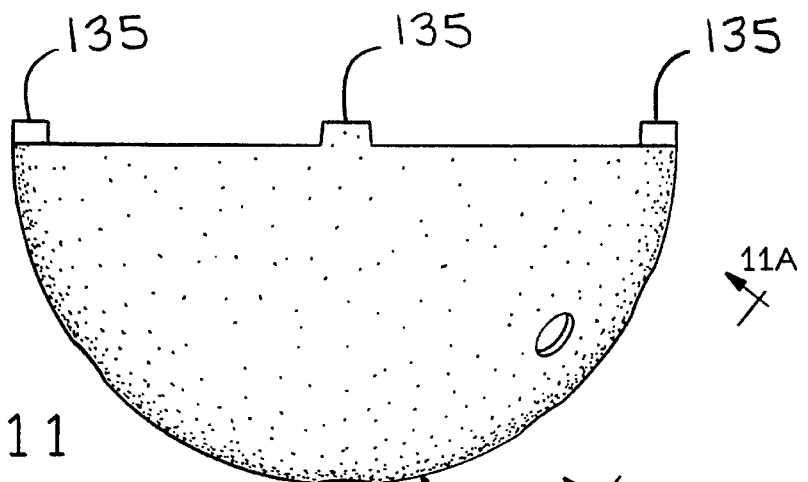
FIG. 11 is an elevational view of a metal shell of the type shown in the FIG. 8 embodiment.
Figure 11A:
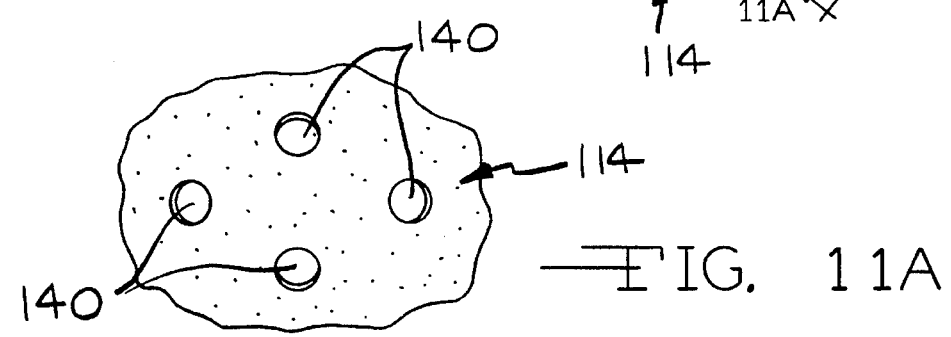
FIG. 11A is a fragmentary view looking in the direction of line 11A—11A of FIG. 11.

Referring now to FIGS. 8–12, there is shown a modified embodiment of the acetabular cup member of the present invention. FIGS. 8–10 show the acetabular cup member 112 assembled in a shell 114 to form an acetabular cup assembly 110. The acetabular cup member 112 may be used as a unitary element and implanted directly in a prepared cavity of an acetabulum using bone cement. As such, the exterior face 118 is provided with grooves 146 separated by ribs 147 and joined together by grooves 148 as in the embodiment of FIGS. 1–7. Additional grooves 149 are also provided on opposite sides of the apex.

Extending outwardly from the exterior face 118 at the edge 124 is a flange 128. The flange 128 is provided with a plurality of slots 129. As shown in FIG. 8, there are four slots 129. There could be a greater number of lesser number of such slots; however, it is greatly preferred that there be at least two such slots 129. The acetabular cup member 112 also has a bead 134 extending around the exterior face 118 in spaced parallel relationship with the flange 128.

In the event it is desired to use the acetabular cup member 112 as a component in an acetabular cup assembly, it will be affixed to a metal shell 114 which is identical to the metal shell 14 of the previous embodiment with the exception that the metal shell 114 has a plurality of upwardly extending lugs 135 which are positioned in spaced apart relationship such that they will engage the slots 129 of the flange 128 when the acetabular cup member 112 is positioned therein. As in the previous embodiment, the bead 134 engages an inwardly facing groove 142 of the metal shell 114. The metal shell 114 also has a plurality of screw receiving apertures 140 and a threaded aperture 142.

Referring now to FIGS. 13–17, there is shown yet another embodiment of acetabular cup assembly 210 and acetabular cup member 212 which may be used as a component for such assembly or as a unitary acetabular cup with no metal shell for direct implantation in cement in the prepared cavity of the acetabulum. Under the embodiment of FIGS. 13–17, the acetabular cup member 212 is provided with an exterior face 218 having grooves 246, 248 and 249 and ribs 247 as in the previous embodiments. It also has an annular flange 228 extending outwardly therefrom at the edge 224. Immediately below the annular flange 228 are a series of sawtooth members 250. Adjacent the sawtooth members 250 on the opposite side thereof from the flange 228 is a screw thread 256. As can be seen from FIG. 13, the sawtooth members 250 are angled in a direction permitting the acetabular cup member 212 to be screwed into a member having a similar sawtooth members but preventing the unscrewing thereof. Preferably, the sawtooth members 250 have rounded ends.

A plurality of recesses 255 are formed in the edge 224. The recesses 255 are positioned such that they may be engaged by a spanner wrench in order to screw the acetabular cup member 212 in position when used with a metal shell.

When the acetabular cup member 21 2 is used as a component of an acetabular cup assembly 210, a metal shell 214 is provided. The metal shell 214 is similar to the metal shell 14 of the embodiment of FIGS. 1–8; however, it is provided with a series of sawtooth members 257 extending around the shell interior 220 in a position to be engaged by the sawtooth members 250 of the acetabular cup member 212. Beneath the sawtooth members 257 of the metal shell 214 is a thread 258 positioned to be engaged by the thread 256 of the acetabular cup member 212. As can be seen from FIG. 13, the angle of the sawtooth members 257 of the metal shell 214 are similar to the angle of the sawtooth members 250 of the acetabular cup member 212 such that the acetabular cup member 212 can be readily screwed into the metal shell 214 due to the resiliency of the plastic material from which the acetabular cup member is made but cannot be removed therefrom.

The sawtooth members 250 and 257 and the threads 256 and 258 are made in such a way as to avoid formation of particulate debris or shredded particles in the course of assembling the acetabular cup member 212 to the shell 214. For example, the sawtooth members 250 and 257 are formed with rounded ends. Additionally, sharp edges are avoided on the threads 256 and 258. It is important to avoid the formation of particulate debris as its formation leads to micromigration thereof which can cause corrosion.

The metal shell 214 is provided with a threaded, dead-end recess 243 at its apex. The threaded recess 243 extends from the interior face 236 through 60% to 80% of the thickness of the shell 214 and is available for use by the surgeon with a threaded tool for insertion of the metal shell 214 during implantation or removal of the metal shell 214 in the event subsequent removal thereof is required.

Figure 12:
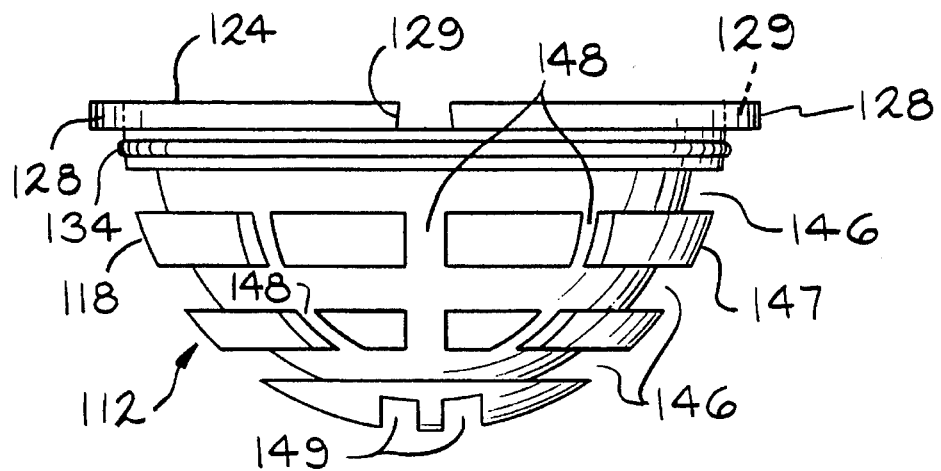
FIG. 12 is an elevational view of a an acetabular cup member of the type used in the FIG. 8 embodiment.
Figure 13:
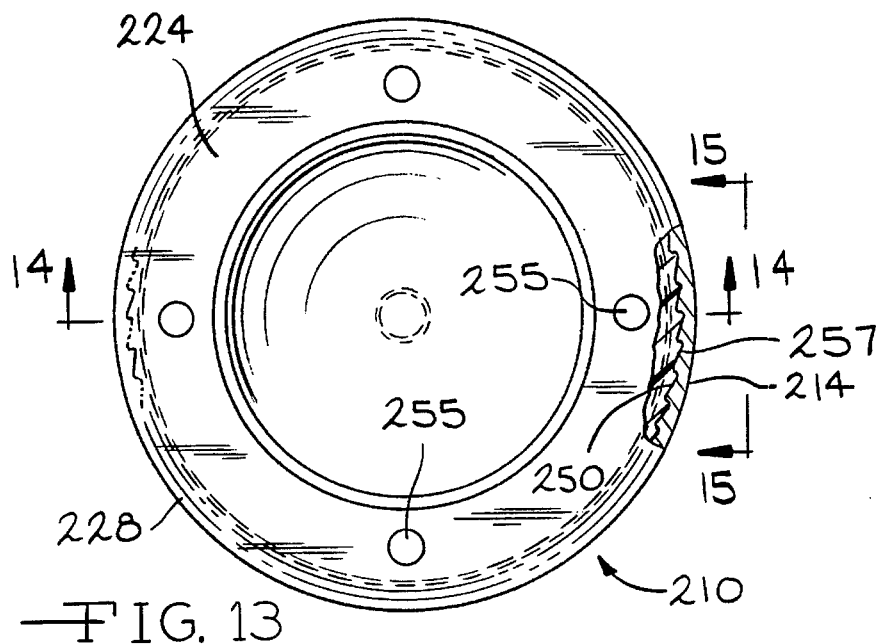
FIG. 13 is a plan view of yet another embodiment of acetabular cup member showing it assembled with a metal shell.
Figure 15:
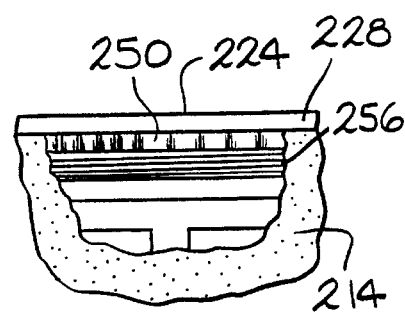
FIG. 15 is an enlarged fragmentary view looking in the direction of the arrows of line 15—15 of FIG. 13.
Figure 14:
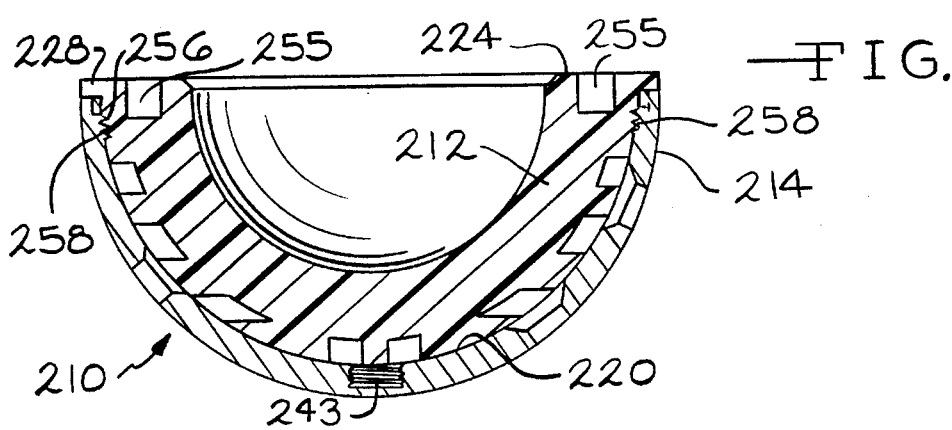
FIG. 14 is a sectional view taken through line 14—14 of FIG. 13.
Figure 16:
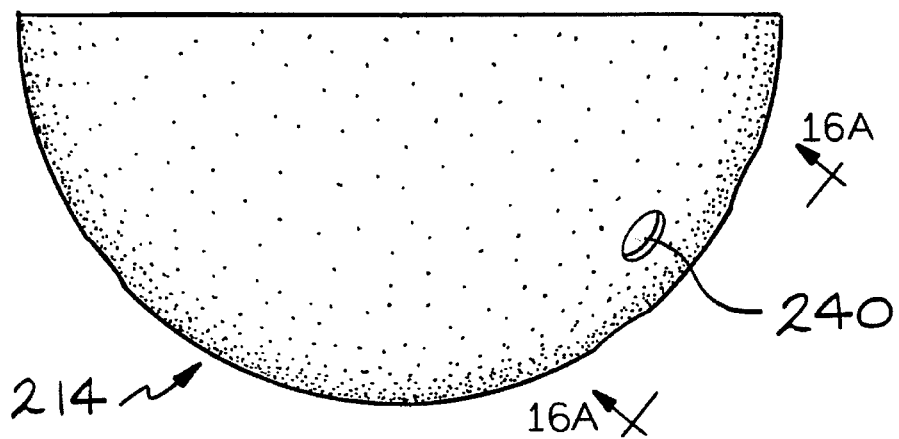
FIG. 16 is an elevational view of a metal shell of the type shown in the FIG. 13 embodiment.
Figure 16A:
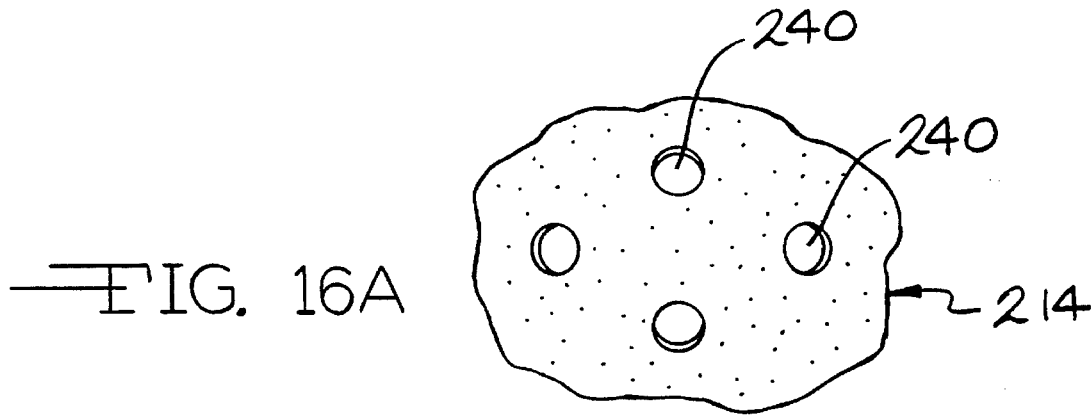
FIG. 16A is a fragmentary view looking in the direction of line 16A—16A of FIG. 16.
Figure 17:
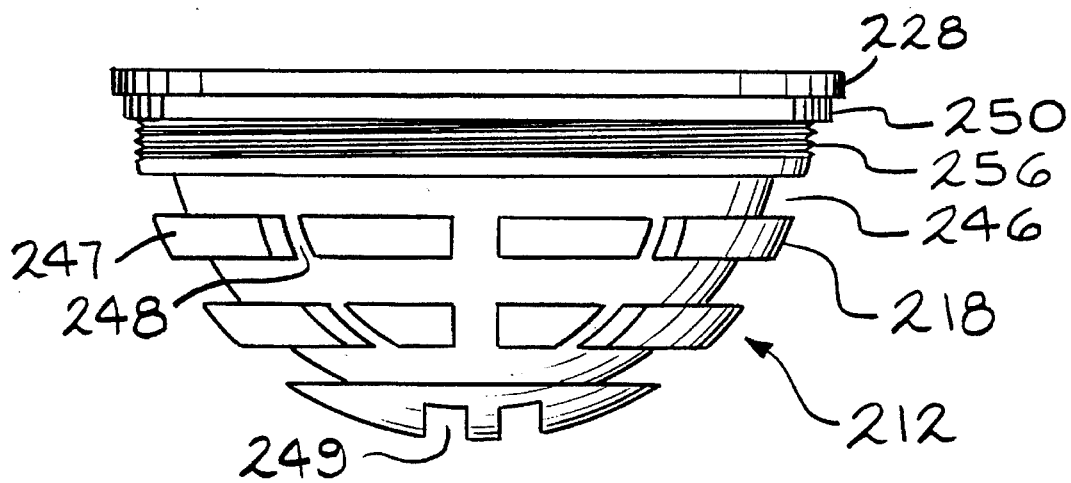
FIG. 17 is an elevational view of the acetabular cup member of the FIG. 13 embodiment.
Figure 18:
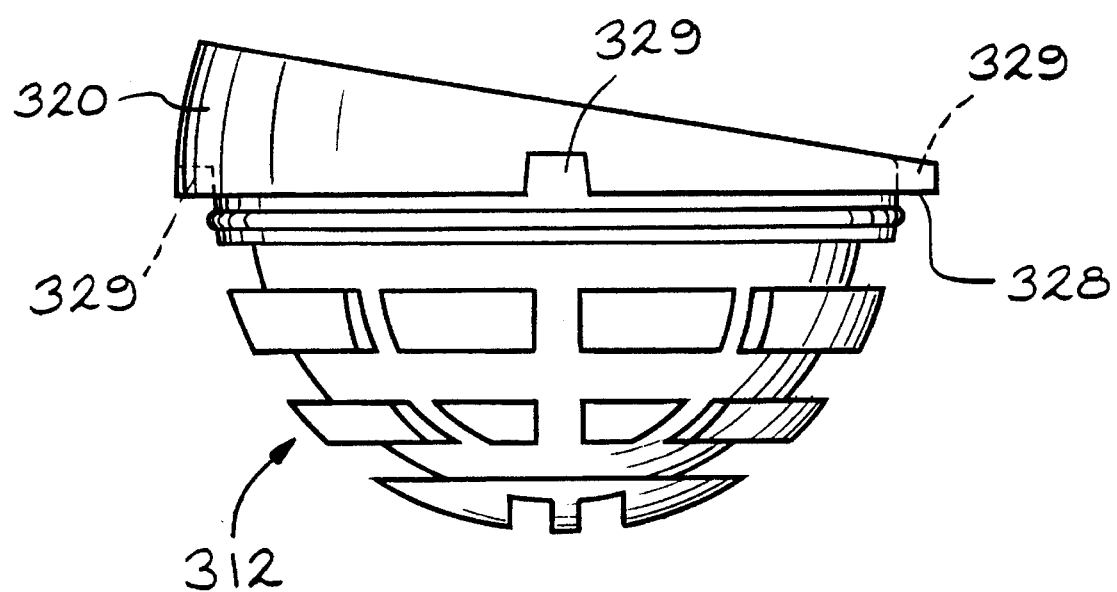
FIG. 18 is an elevational view of another embodiment of the acetabular cup member.

Referring now to FIG. 18, there is provided yet another embodiment of acetabular cup member 312 which is identical to the acetabular cup member 112 of FIG. 12 with the exception that it is provided with an extended rim 320 which extends upwardly from the flange 328 at an angle of 5° to 10° from the lower surface of the flange 328 as viewed in FIG. 18. A plurality of slots 329 extend into the flange and, if desired into the extended rim 320. This embodiment is provided for surgeons who prefer to use acetabular cup members having extended rims. It should be recognized that extended rims could be used with the other embodiments of the present invention. Extended rims are well known and, in and of themselves, form no part of the present invention.

The acetabular cup member of the present invention provides a significant cost benefit in that a single acetabular cup member can be used either as a unitary acetabular cup implanted directly into the prepared cavity of an acetabulum with bone cement where the condition of the patient warrants and yet may also be used as a component with an appropriate metal shell where the condition of the patient requires the use of an acetabular cup assembly.

Many modifications of the present invention will become readily apparent to those skilled in the art. For example, among other readily apparent changes, the embodiment of FIGS. 13–17 shows the sawtooth members 250 between the flange 224 and the screw thread 256. If desired, the acetabular cup member 212 could be designed with the screw thread 256 between the flange 228 and the sawtooth members 250 provided, of course, that the metal shell 214 were designed with its screw thread 258 and sawtooth members 257 appropriately repositioned.

Referring now to FIGS. 19–22, there is provided an plastic acetabular cup member 112' which, for the purposes of this continuation-in-part patent application is shown as similar but not necessarily identical to the acetabular cup member 112 of the embodiment of FIGS. 8–12. However, it could have a configuration similar to one of the acetabular cup members of the other embodiments of FIGS. 1–7 and 13–18 or a significantly different configuration. As mentioned in the parent application, the acetabular cup member 112' may be used in combination with a metal shell 114 shown in phantom lines in FIG. 21 or it may be cemented directly in the prepared cavity of the acetabulum with bone cement. Under the present invention there is provided a preformed insert 60 which functions as a groove filler for plastic acetabular cup member 112'. Although not essential, it is preferred that the preformed insert 60 be formed of the same material as the acetabular cup member 112'. The preformed insert 60 is intended for use when the plastic acetabular cup member 112' is used in combination with a metal shell 114. The preformed insert 60 is not intended to be used when the acetabular cup member is cemented directly in the prepared cavity. The present invention is also directed to the combination of the preformed insert 60 and the acetabular cup member 112' and to the combination of those with the metal shell 114.

The acetabular cup member 112' includes a planar edge 124' which is joined to the spherical-shaped interior face 120' by a champfer 126'. The interior face 120' has an apex 122' lying on the axis X. Preferably, the planar edge 124' extends beyond the exterior face 118' to form a flange 128' which extends annularly around the exterior face 118' except for four slots 129'. The exterior face 118' of the plastic acetabular cup member 112' has an outwardly extending annular bead 134' for affixing the cup member 112' to the metal shell 114. Additionally, the acetabular cup member 112' has a series of rows of annular grooves 146' which are substantially perpendicular to the axis X and are separated by ribs 147'. Rows of grooves 148' extend toward the apex 122' and define planes which extend through the axis X. Additional grooves 149' may be formed adjacent the apex of the exterior face 118'.

When the acetabular cup member 112' is used in combination with the metal shell 114, it will be subjected to compressive forces imparted by the weight of the patient in whom it is implanted with such compressive forces being of variable magnitude at various portions of the interface between the interior of the metal shell 114 and those portions of the exterior face 118' contacting the interior surface of the metal shell 114. As will be appreciated, it is those portions of the exterior face 118' which are defined by the ribs 147', the areas 159' between the apex and the groove 146' closest to the apex and the area between the additional grooves 149' which engage the interior surface of the metal shell 114 and which are, therefor, subjected to the compressive forces. Such compressive forces may cause the plastic material to creep thus deforming the ribs 147', the areas 159' and the area between the additional grooves 149' and causing cold flow of plastic partially into the grooves 146', 148' and 149'.

Under the present invention, a pair of molded insert members 60 are attached to the acetabular cup member 112' in snug engagement within the grooves 146', 148' and 149' and provide support for the ribs 147', area 159' and other areas to prevent any significant creep or cold flow of the plastic into the grooves 146', 148' and 149'.

The molded insert members 60 have a hemispherical configuration and comprise a series of arcuate ribs 61 defining parallel rows with each row of ribs 61 being sized, shaped, and positioned to snugly fit within one of the three rows of grooves 146' of the acetabular cup member 112'. The rows of parallel ribs 61 are joined together by end ribs 62, intermediate ribs 63 and a central rib 64, each of which lies on a plane extending through the axis X. Adjoining groups of ribs 62, 63 and 64 cooperate to define apertures 68. The intermediate ribs 63 and central ribs 64 are sized to substantially fill the grooves 148' while the end ribs 62 are sized to fill approximately one-half the width of the grooves 148' such that the end ribs 62 of the adjoining two semi-circular insert members 60 will fill a single groove 148'. The apertures 68 are sized to snugly receive the ribs 147' of the acetabular cup member 112'.

The central rib 64 of each insert member 60 extends to an end 69. When the insert members 60 are affixed to the acetabular cup member 112', the respective ends 69 will abut one another at the apex lying on the axis X. In contrast, the intermediate ribs 63 and end ribs 62 extend only between the lower and upper arcuate ribs 61. Extending outwardly from each of the central ribs 64 in an area spaced slightly from the end 69 are a pair of arm members 66 intended to fit within the additional grooves 149'.

Figure 22:
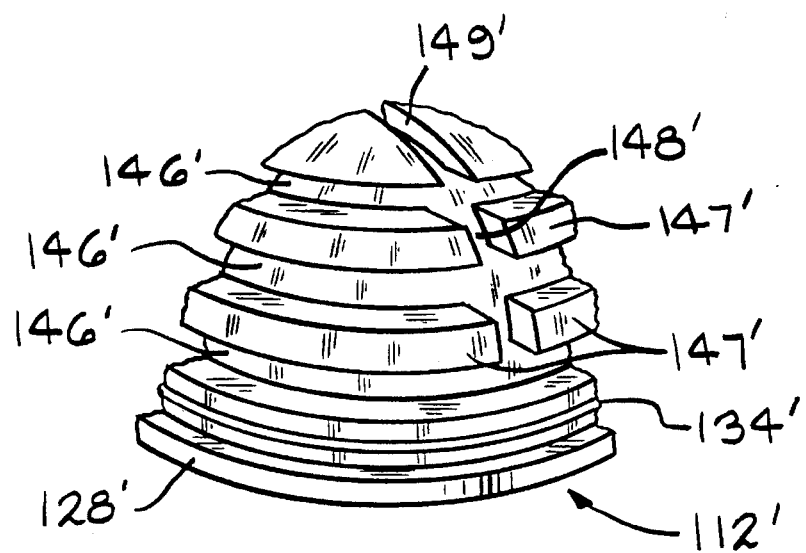
FIG. 22 is a fragmentary perspective view of the plastic acetabular cup member.
Figure 23:
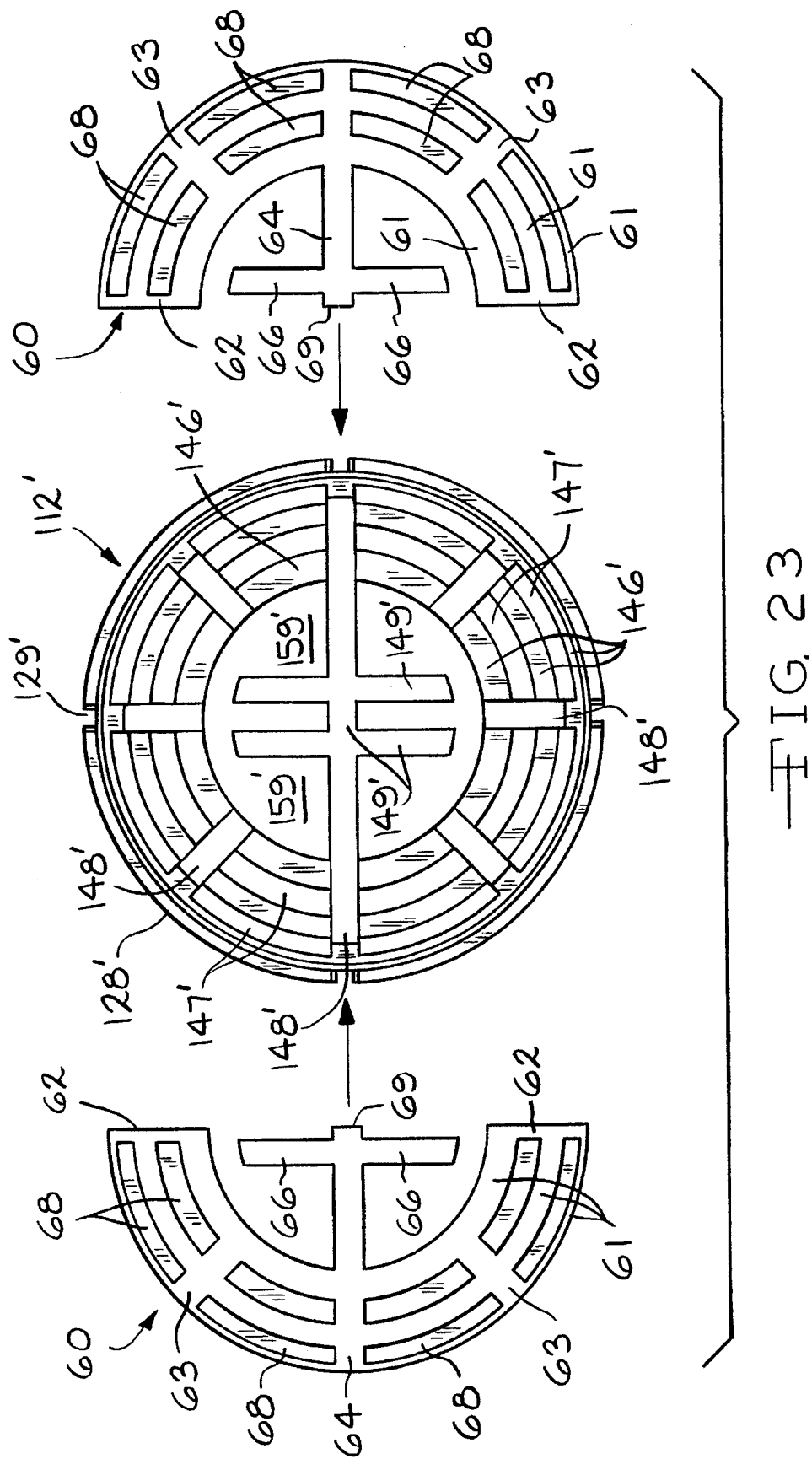
FIG. 23 is an exploded view showing the plastic acetabular cup member as viewed from the dome with the two pre-molded insert members separated therefrom.

As can be readily seen from FIG. 22, the pre-molded inserts 60 may be joined to the acetabular cup member 112' simply by snapping the respective ribs 61, 62, 63 and 64 and arm member 66 in the corresponding grooves of the acetabular cup member 112' and with each of the end ribs 62 of one insert 60 abutting one of the end ribs 62 of the other insert 60.

If desired, rather than two hemispherically-shaped inserts 60 there may be provided three or four or even more pre-molded inserts, each extending a smaller arcuate length than each of the inserts 60. Such greater number of inserts should, of course, be sized to cooperate to substantially fill all of the grooves 146', 148' and 149' when attached to the acetabular cup member 112'. Additionally there could be provided a single pre-molded insert with the parallel rows of arcuate ribs corresponding to the rows of arcuate ribs 61 extending 360°. In that event, it may be desirable that one of the ribs corresponding to a central rib be split so that the insert may be opened slightly during affixing to the acetabular cup member 112'.

Figure 19:
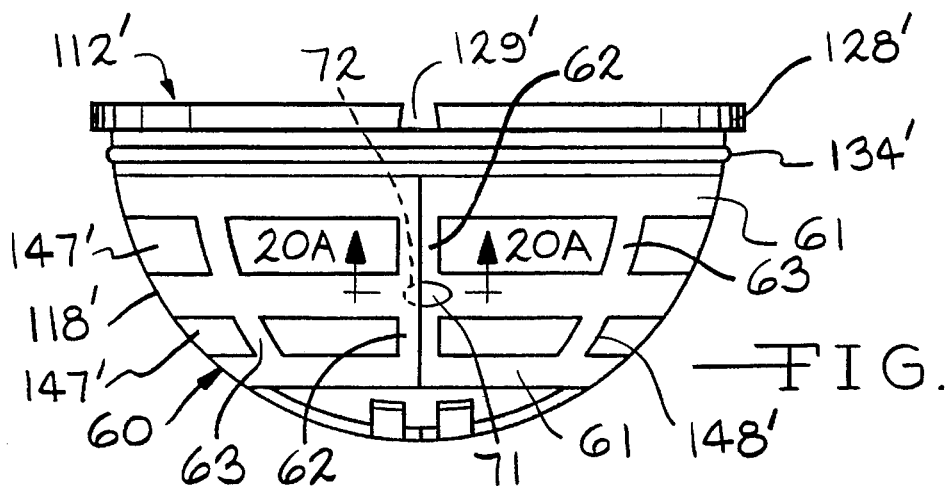
FIG. 19 is an elevational view of a plastic acetabular cup member having grooves and having a pair of pre-molded insert members positioned in said grooves.
Figure 20:
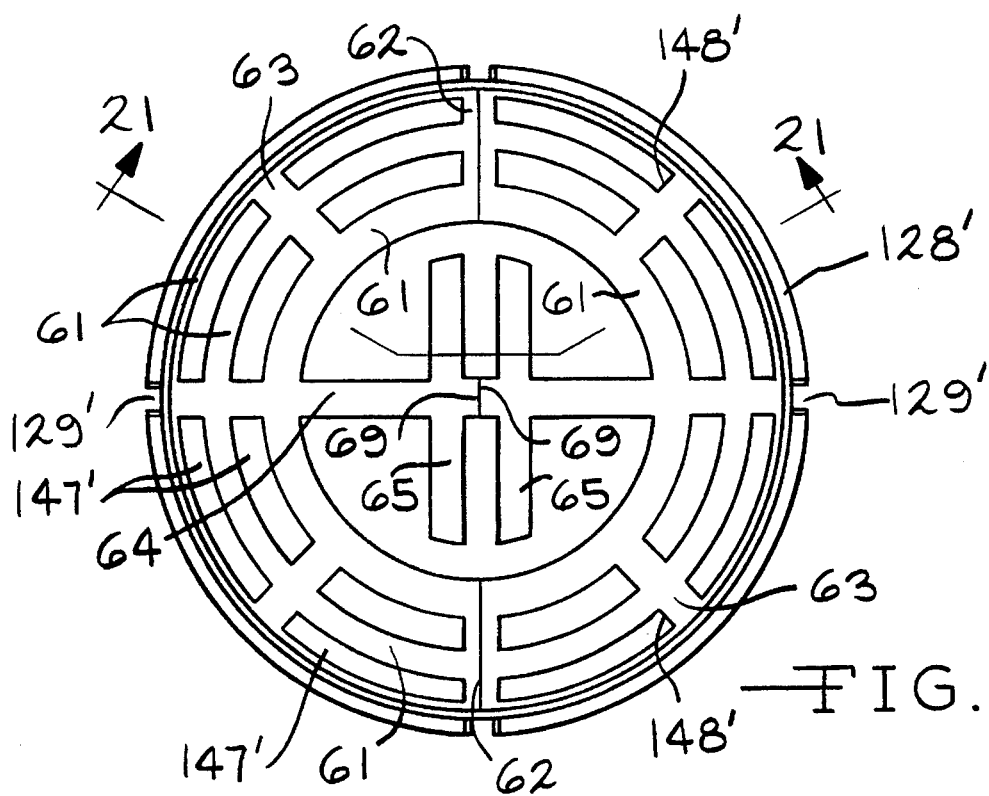
FIG. 20 is a top plan view of such plastic acetabular cup member with the pre-molded insert as viewed from the top or dome thereof.
Figure 20A:
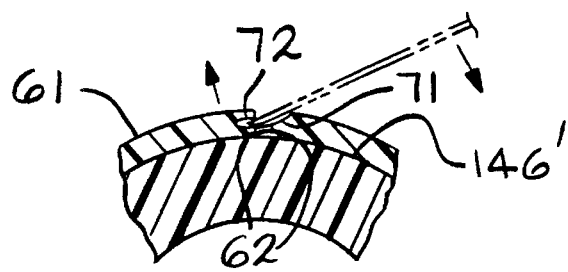
FIG. 20A is a sectional view taken through line 20A—20A of FIG. 19 and showing in phantom lines a tool to assist in removing an insert member from the grooves.
Figure 21:
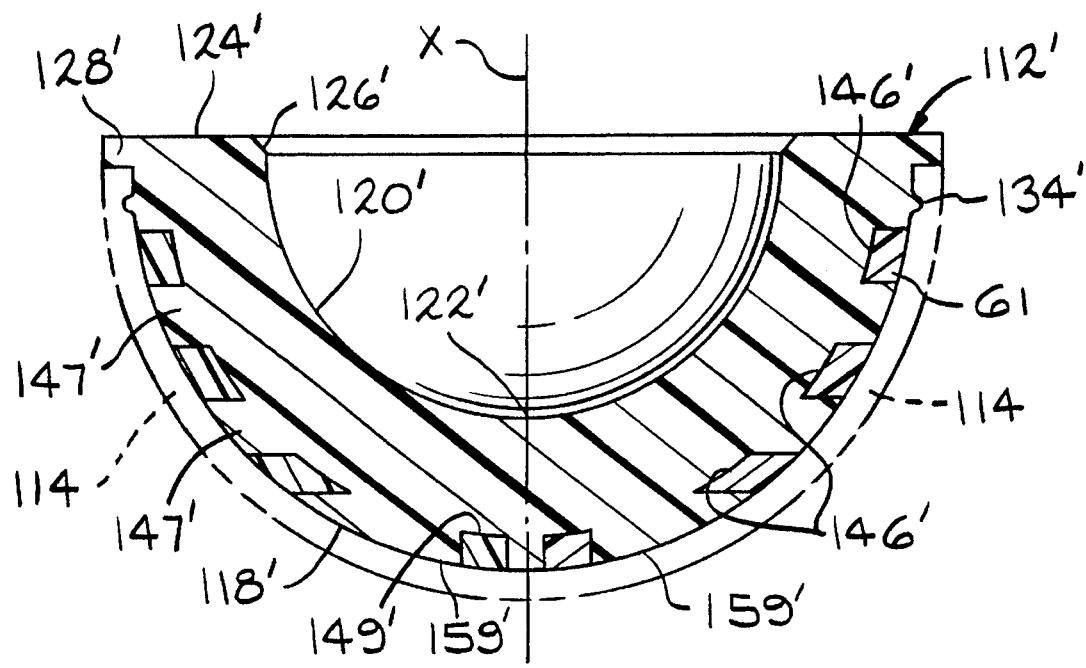
FIG. 21 is a sectional view taken through line 21—21 of FIG. 20.

Referring now to FIGS. 19 and 20A, there is shown an optional feature which may be provided in order to assist the surgeon in removing the pre-molded insert members 60 from the acetabular cup member 112' if it is desired to use the acetabular cup member 112' for direct implantation in cement, i.e., without use of a metal shell. As shown in FIGS. 19 and 20A, one of the end ribs 62 of at least one and preferably both insert members 60 is provided with a recess 71 or groove in its outer surface and the adjacent end rib 62 of the opposing insert member 60 is provided with a detent 72 extending inwardly from the edge 62 in an area aligned with the recess 71. With this feature, a surgeon who wishes to remove the insert members 60 can simply position a lever in the recess 71 of one insert member 60 and slide it forward so its end extends into the detent 72 of the opposing insert member 60 and, using such lever, pry such opposing insert member 60 out of the grooves.

Many other modifications will be readily apparent to those skilled in the art. Accordingly, the scope of the present invention should be limited only by the scope of the appended claims.

I claim:

1. An acetabular cup assembly comprising:

(a) metal shell with an interior surface having a generally dome shaped configuration:

(b) a plastic acetabular cud member having a smooth interior surface with a generally spherical shape and an exterior surface with a plurality of grooves and ribs, said ribs having said outer surface areas in contact with said metal shell interior surface, a major portion of said grooves being interconnected, including outer surface areas engaged to said metal shell interior surface and inner surface areas spaced from said metal shell interior surface and cooperating therewith to define cavities; and (c) at least two insert members positioned in and filling substantially all of said cavities.

2. The acetabular cup assembly of claim 1, wherein said acetabular cup member lies on an axis and said grooves include a first set of grooves substantially perpendicular to said axis and a second set of grooves, each of said second set lying in a plane passing through said axis.

3. The acetabular cup assembly of claim 2, wherein each of the grooves of said second set of grooves has a predetermined width which is substantially the same as the width of each of the other grooves of said second set.

4. The acetabular cup assembly of claim 3, wherein said insert members include a first set of ribs positioned in said first set of grooves and a second set of ribs positioned in said second set of grooves.

5. The acetabular cup assembly of claim 4, wherein each of said insert member second set of ribs includes a pair of end ribs, said end ribs having a width approximately one-half the width of the other ribs of said second set.

6. The acetabular cup assembly of claim 5, wherein an end rib of one insert member is positioned in the same groove as an end rib of another insert member.

7. The acetabular cup assembly of claim 6, wherein one of said end ribs has an outer surface and a recess extending inwardly from said outer surface.

8. The acetabular cup assembly of claim 7, wherein one of said end ribs has a detent aligned with a recess of an adjoining end rib.

9. An acetabular cup assembly comprising:
   (a) a metal shell with an interior surface having a generally dome shaped configuration;
   (b) a non-metallic acetabular cup member having a smooth interior surface with a generally spherical shape and an exterior surface with a plurality of grooves and ribs, said ribs including outer surface areas engaged to said metal shell interior surface, inner surface areas spaced from said metal shell inter surface, walls between said outer surface areas and said inner surface areas, said walls and said inner surface areas cooperating to define cavities; and,
   (c) insert members positioned in and filling substantially all of said cavities.

10. The acetabular cup assembly of claim 9, wherein said insert members engage said metal shell interior surface.

11. The acetabular cup assembly of claim 9, wherein a major portion of the grooves are interconnected.

12. An acetabular cup assembly comprising:
   (a) a metal shell with an interior surface having a generally dome shaded configuration;
   (b) a non-metallic acetabular cup member having a smooth interior surface with a generally spherical shape and an exterior surface with a plurality of grooves and ribs, said ribs including outer surface areas engaged to said metal shell interior surface, a major portion of the grooves being interconnected, inner surface areas spaced from said metal shell inter surface, walls between said outer surface areas and said inner surface areas, said walls and said inner surface areas cooperating to define cavities; and,
   (c) at least two insert members positioned in and filling substantially all of said cavities.

13. The acetabular cup assembly of claim 9, wherein said acetabular cup member lies on an axis and said grooves include a first set of grooves substantially perpendicular to said axis and a second set of grooves, each of said second set lying in a plane passing through said axis.

14. The acetabular cup assembly of claim 13, wherein each of the grooves of said second set of grooves has a predetermined width which is substantially the same as the width of each of the other grooves of said second set.

15. An acetabular cup assembly comprising:
   (a) a metal shell with an interior surface having a generally dome shaded configuration;
   (b) a non-metallic acetabular cup member lying on an axis having a smooth interior surface with a generally spherical shade and an exterior surface with a plurality of grooves and ribs, said grooves including a first set of grooves substantially perpendicular to said axis and a second set of grooves, each of said second set lying in a plane passing through said axis, and having a predetermined width which is substantially the same as the width of each of the other grooves of said second set, said ribs including outer surface areas engaged to said metal shell interior surface, inner surface areas spaced from said metal shell inter surface, walls between said outer surface areas and said inner surface areas, said walls and said inner surface areas cooperating to define cavities; and,
   (c) insert members including a first set of ribs positioned in said first set of grooves and a second set of ribs positioned in said second set of grooves.

16. The acetabular cup assembly of claim 15, wherein each of said insert member second set of ribs includes a pair of end ribs, said end ribs having a width approximately one-half the width of said second set of grooves and an end rib of one insert member is positioned in the same groove as an end rib of another insert member.

17. The acetabular cup assembly of claim 16, wherein one of said end ribs has an outer surface and a recess extending inwardly from said outer surface.

18. The acetabular cup assembly of claim 17, wherein one of said end ribs has a detent aligned with a recess of an adjoining end rib.

19. An acetabular prosthesis comprising in combination:
   (a) a metal shell having a cup-shaped interior surface extending from an apex to an edge;
   (b) a non-metallic cup member having a central axis, an inner face with a generally done-shaped configuration extending from an apex lying on said axis and an outer portion opposite said inner face engaged to said metal shell interior surface, said outer portion having formed therein a series of recesses; and
   (c) groove insert members positioned in and substantially filling said recesses.

20. The prosthesis of claim 19, wherein said groove inserts engage said shell interior surface.

* * * * *

UNITED STATES PATENT AND TRADEMARK OFFICE
CERTIFICATE OF CORRECTION

PATENT NO. : 5,480,448
DATED : January 2, 1996
INVENTOR(S) : W.E. Michael Mikhail It is certified that error appears in the above—identified patent and that said Letters Patent is hereby corrected as shown below:

Col. 8, line 44, delete "cud" and insert --cup--.
Col. 9, line 35, delete "shaded" and insert --shaped--.
Col. 10, line 7, delete "shaded" and insert --shape --.
Col. 10, line 10, delete "shade" and insert --shaped--.

Signed and Sealed this

Twenty-third Day of July, 1996

Attest:

BRUCE LEHMAN

Attesting Officer   Commissioner of Patents and Trademarks